United States Patent [19]

Kyle

[11] Plant 4,088

[45] Aug. 2, 1977

[54] ROSE PLANT

[75] Inventor: Thomas B. Kyle, Tipp City, Ohio

[73] Assignee: Spring Hill Nurseries Co., Tipp City, Ohio

[21] Appl. No.: 711,361

[22] Filed: Aug. 3, 1976

[51] Int. Cl.[2] ..... A01H 5/00

[52] U.S. Cl. ..... Plt./5

[58] Field of Search ..... Plt./5, 2

*Primary Examiner*—Robert E. Bagwill

*Attorney, Agent, or Firm*—Vincent G. Gioia

[57] ABSTRACT

This invention relates to a climbing mutation of Kolner Karneval.

1 Drawing Figure

1

The present invention relates to a new and distinct variety of climbing rose which is a mutation (sport) of the hybrid tea rose known as "Kolner Karneval" (also known as "Blue Girl"). The present variety continues the advantageous and desirable qualities of the variety of which it is a mutation, notably in flower and foliage characteristics, but exhibits growth characteristics different therefrom and which are typical of roses of the climbing rose class.

Among the novel characteristics possessed by this new variety which distinguish it from the variety from which it is a mutation and all other varieties of which I am aware are: (1) strong canes of vigorous growth capable of attaining 10 and 12 feet in length in the first growing season and (2) flower form and foliage of the original variety, i.e., bluish lavender-pink coloring displaying pleasing bluish silver tones at the heart of the flowers combining with abundant, large, deep green, glossy, thick foliage. Asexual reproduction by budding of the new variety as performed in Miami County, Ohio, shows that the foregoing and other distinguishing characteristics come true to form and are established and transmitted through succeeding propagations.

The new and improved rose variety was discovered by me among plants grown at Spring Hill Nurseries, Tipp City, Ohio, under my supervision. It is a profuse bloomer and produces flowers both singly and in cluster on a recurring basis throughout the growing season. The many-petaled flowers are of good hybrid tea form and are also unusually large, i.e., 5 to 5½ inches.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "58B" is plate 58B of the Royal Horticultural Society Color Chart.

Mutation of: Kolner Karneval (Blue Girl) — Hybrid tea rose.

Type: Climbing hybrid tea.

2

FLOWER

Blooming Habit: Continuous.

Bud:

*Size.*—Large.

*Form.*—Initially ovoid then high centered with petals recurling freely.

*Color.*—When sepals first divide — RHS 58B. When petals begin to unfurl — RHS 70D. When half-blown: Inside of petals — RHS 65A to 65B; reverse side of petals — blending between RHS 65C to 70D.

*Sepals.*—Glabrous, short, pointed — do not extend beyond bud.

*Peduncle.*—Length — 2 to 2½ inches. Aspect — rounded, slight curve at base. Strength — erect, strong. Color — RHS 173A.

Bloom:

*Size.*—Average size when fully expanded — 5½ to 6 inches.

*Borne.*—Singly and several together.

*Form.*—High centered at first, petals rolled outward becoming ruffled at maturity.

*Petalage.*—Number of petals under normal conditions — about 43 to 46.

*Color (during first two days).*—Inner petals at center of flower — RHS 70D. Outer petals — RHS 69A. Base of petals (point of attachment) — RHS 58D. Reverse of petals — RHS 67D. General tonality from a distance — soft purple pink with deeper bluish silver tones in the heart of the flowers.

*Color Change.*—As bloom ages flower fades to near RHS 67D then to RHS 69A.

Petals:

*Texture.*—Thick.

*Appearance.*—Inside: Satiny crisp. Outside: Petal smooth with slight gloss.

*Form.*—Rounded, tapered to base.

*Arrangement.*—Imbricated, regularly arranged shingle-like.

*Petaloids in Center.*—Few.

*Persistence.*—Drop off clean.

*Fragrance.*—Slight old rose.

*Lasting Quality.*—Very long lasting on bush and when cut.

REPRODUCTIVE ORGANS

Stamens, filaments and anthers:
*Arrangement.*—Regularly arranged around styles.
*Color.*—Bronze yellow.
Pollen:
*Color.*—Deep yellow.
Styles: Bunched and of medium length.
Stigmas:
*Color.*—Near RHS 168B.
Hips:
*Shape.*—Globular.
*Size.*—Large.
*Color.*—RHS 169B.
*Do seeds protude.*—Seed usually contained in hip.

PLANT

Form: Spreading and upright.
Growth: Very vigorous. Height attained — 10 to 12 feet in first season.
Foliage: Compound of 5 to 7 leaflets
*Size.*—Large.
*Quantity.*—Abundant.
*Color.*—New foliage: upper side — deep green with red bronze cast; under side — deep wine red. Old foliage: upper side — deep green with RHS 185A cast; under side — near to RHS 184A.
*Shape.*—Oval, pointed.
*Texture.*—Upper side — glossy, thick. Under side — dull, smooth.
*Edge.*—Almost smooth.
*Serration.*—Single, small.

*Leaf stem.*—Color — RHS 185A. Under side — RHS 184A.
*Stipules.*—Medium length.
*Resistance to disease.*—Blackspot — Very good. Mildew — Good. Rust — Good.
Wood:
*New wood.*—Color — RHS 139C with RHS 182A streaking. Bark — smooth.
*Old Wood.*—Color — RHS 138C. Bark — smooth.
Thorns:
*Thorns.*—Quantity: on main stalks from base — ordinary. On laterals from stalk — few. Form — flat. Length — medium. Color (when young) — RHS 139B. Position — irregular.
*Prickles.*—Quantity: on main stalks — few. On laterals — none.
Winter Hardiness: Winter hardy.

I claim:

1. A new and distinct variety of climbing rose plant substantially as shown and described, which is a mutation of the hyrid tea rose known as "Kolner Karneval" (also known as "Blue Girl"), characterized particularly by strong canes of vigorous growth capable of attaining a length of 10 to 12 feet in the first growing season and flower form and foliage of the original variety, i.e., bluish lavender-pink coloring displaying pleasing bluish silver tones at the heart of the flowers combining with abundant, large, deep green, glossy, thick foliage, on a vigorous profusely blooming plant bearing flowers both singly and in clusters on a recurring basis throughout the growing season.

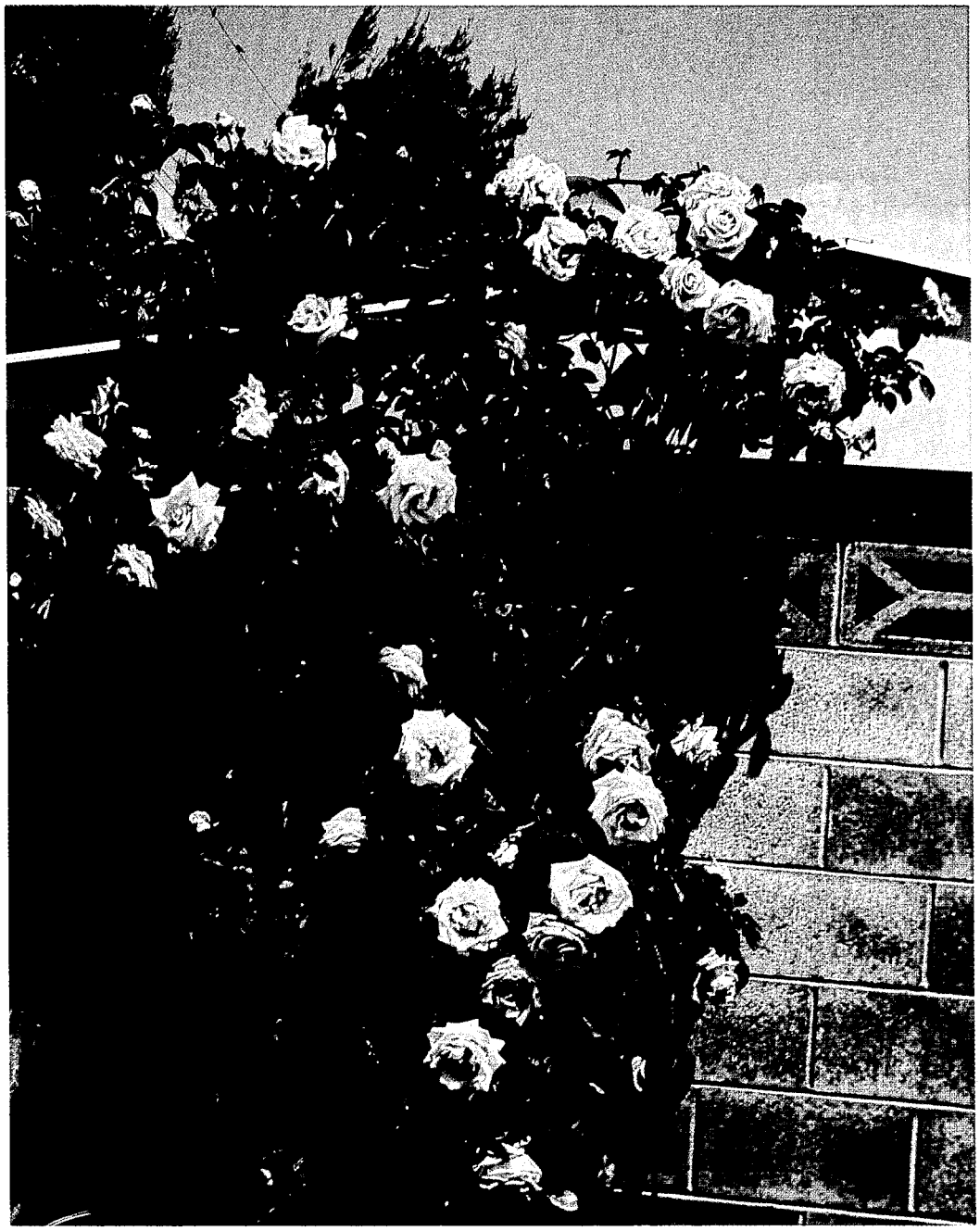

* * * * *